(12) United States Patent
Ouse et al.

(10) Patent No.: US 8,835,357 B2
(45) Date of Patent: Sep. 16, 2014

(54) AGRICULTURAL COMPOSITIONS COMPRISING OIL-IN-WATER EMULSIONS

(75) Inventors: David G. Ouse, Indianapolis, IN (US); Holger Tank, Zionsville, IN (US); Wen Xu, Cary, NC (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/349,171

(22) Filed: Jan. 12, 2012

(65) Prior Publication Data

US 2012/0184441 A1    Jul. 19, 2012

Related U.S. Application Data

(60) Provisional application No. 61/432,878, filed on Jan. 14, 2011.

(51) Int. Cl.
| | |
|---|---|
| *A01N 43/40* | (2006.01) |
| *A01N 37/10* | (2006.01) |
| *A01N 25/04* | (2006.01) |
| *A01N 25/28* | (2006.01) |

(52) U.S. Cl.
CPC ............... *A01N 25/04* (2013.01); *A01H 43/40* (2013.01); *A01N 25/28* (2013.01)
USPC ............................. 504/254; 504/260; 504/321

(58) Field of Classification Search
None
See application file for complete search history.

(56) References Cited

U.S. PATENT DOCUMENTS

| | | | |
|---|---|---|---|
| 2009/0197768 A1 | 8/2009 | Boucher et al. | |
| 2009/0247409 A1* | 10/2009 | Xu et al. | 504/320 |
| 2013/0079410 A1 | 3/2013 | Omura et al. | |

OTHER PUBLICATIONS

Stepan Company, "Toximul® 8323", <http://www.jazdchemicals.com/chemyellowpages/company/Stepan-Company/TOXIMUL-8323.htm?supplierId=13653279&productId=140705>, copyright 2013, p. 1.*
Ist, "The HLB System for Selecting Emulsifiers," <http://web.ist.utl.pt/~ist11061/fidel/creac/sec36b.html>, accessed Jan. 10, 2014, p. 1-2.*
International Searching Authority, International Search Report for PCT/US2012/21075, Apr. 20, 2012.

* cited by examiner

*Primary Examiner* — Tracy Vivlemore
*Assistant Examiner* — Monica Shin
(74) *Attorney, Agent, or Firm* — C. W. Arnett; Faegre Baker Daniels LLP

(57) ABSTRACT

The present invention relates to an oil-in-water emulsion, comprising oily globules that include at least one agriculturally active ingredient, in which the oily globules of the emulsion and are coated with a polymeric adsorption layer. The polymeric adsorption layer coating the oily globules includes (1) at least one polymeric surface-active agent having an HLB values in the range of about 16 to about 18, and (2) at least one ionic surface-active agent. The oily globules of the emulsion have mean particle diameter of less than about 800 nanometers, are resistant to Ostwald ripening and are well suited for the treatment of plants. Agriculturally active ingredients that can be used with the emulsion include, pesticides, herbicides, fungicides, mitocides, bactericides and the like. The invention further includes methods of using the inventive oil-in-water emulsions to treat plants and on surfaces adjacent to plants, plant pests or other pests.

25 Claims, No Drawings

AGRICULTURAL COMPOSITIONS COMPRISING OIL-IN-WATER EMULSIONS

CROSS REFERENCE TO RELATED APPLICATIONS

This application claims the benefit of U.S. Provisional Patent Application Ser. No. 61/432,878 filed Jan. 14, 2011, which is incorporated herein by reference in its entirity.

FIELD OF THE INVENTION

The present invention relates to stable, agricultural oil-in-water emulsion compositions.

BACKGROUND

Concentrated oil-in water emulsions of liquid active ingredients or active ingredients dissolved in a solvent are commonly used in agricultural compositions due to certain advantages provided over other formulation types. Emulsions are water based, contain little or no solvent, allow mixtures of active ingredients to be combined into a single formulation and are compatible with a wide range of packaging material. However, there are also several disadvantages of such agricultural emulsions, for example, they are often complex formulations which require high amounts of surface-active agents for stabilization, are generally very viscous, have a tendency for Oswald ripening of the emulsion globules and separate over time. Therefore, improvements in such emulsion formulations are needed in the agricultural field.

Several oil-in-water emulsion compositions for cosmetics and dermatological applications have been described in patents U.S. Pat. Nos. 5,658,575; 5,925,364; 5,753,241; 5,925,341; 6,066,328; 6,120,778; 6,126,948; 6,689,371; 6,419,946; 6,541,018; 6,335,022; 6,274,150; 6,375,960; 6,464,990; 6,413,527; 6,461,625; and 6,902,737; all of which are incorporated herein by reference. However, although these types of emulsions have found advantageous use in personal care products, these types of emulsions have not been widely used with agriculturally active compounds, which are typically present in emulsions at much higher levels than cosmetic active ingredients.

SUMMARY

Some embodiments of the invention include an oil-in-water emulsion composition having at least one agriculturally active compound, the oil-in-water emulsion composition comprising: A) an oil phase, wherein the oil phase includes at least one agriculturally active ingredient, and is comprised essentially of oily globules, the oily globules having a mean particle diameter of less than about 800 nanometers; and B) an aqueous phase, wherein the oily globules are dispersed in the aqueous phase and wherein at least some of the oily globules dispersed in the aqueous phase are coated with a polymeric adsorption layer, wherein said polymeric adsorption layer comprises: (1) at least one polymeric surface-active agent having an HLB value in the range of about 16 to about 18; and (2) at least one ionic surface-active agent. In some embodiment the aqueous phase includes a second polymeric surface active agent having an HLB in the range of about 12 to about 14. In some embodiments the polymeric surface-active agent is selected from the group consisting of: amphipathic block and graft copolymers.

In some embodiments the aqueous phase includes a non-ionic, non-polymeric surface active agent. In some embodiments the ionic surface-active agent in the composition is selected from the group consisting of: (a) neutralized anionic surface-active agents, (b) amphoteric surface-active agents, (c) alkylsulphonic derivatives and (d) cationic surface-active agents.

In some embodiments the ionic surface-active agent in the composition is selected from the group consisting of: alkali metal salts of dicetyl phosphate and dimyristyl phosphate, in particular sodium and potassium salts; alkali metal salts of cholesteryl sulphate and cholesteryl phosphate, especially the sodium salts; lipoamino acids and their salts, such as mono- and disodium acylglutamates, such as the disodium salt of N-stearoyl-L-glutamic acid, the sodium salts of phosphatidic acid; phospholipids; the mono- and disodium salts of acylglutamic acids, in particular N-stearoylglutamic acid; and alkyl ether citrates. In some embodiments the composition of Claim 4, wherein the ionic surface-active agent is a phospholipid. In some embodiments the ionic surface-active agent is an alkylsulphonic derivative. And in some embodiments the ionic surface-active agent is selected from the group consisting of quaternary ammonium salts, fatty amines and salts thereof.

In some embodiments of the invention the amount of the polymeric surface-active agents (1) in the composition is in the range of about 30 to about 95 wt. % of the total of both (1) and (2). In still other embodiments of the invention the amount of the polymeric surface-active agents (1) in the composition is in the range of about 50 to about 95, weight percent of the total of both (1) and (2). And in still other embodiments of the invention the amount of the ionic surface active agent (2) in the composition is in the range of about 5 to about 50 wt. % of the total combined weight of (1) and (2).

In some embodiments of the invention the amount of the ionic surface active agent (2) in the composition is in the range of about 10 to about 50 wt. % of the total combined weight of (1) and (2).

In some embodiments of the invention the coating on the oily globules comprises between about 0.5 wt. % to about 20 wt. % based on the total weight of the oil-in-water emulsion. In still other embodiments the coating on the oily globules comprises between about 0.5 wt. % to about 10 wt. % based on the total weight of the oil-in-water emulsion. While in still other embodiments the coating on the oily globules comprises between about 0.5 wt. % to about 2.5 wt. % based on the total weight of the oil-in-water emulsion.

In some embodiments of the invention the oil-in-water emulsion in the composition includes at least one agriculturally active ingredient selected from the group consisting of: fungicides, insecticides, nematocides, miticides, biocides, termiticides, rodenticides, arthropodicides, herbicides, bactericides, and bacteria stats.

In some embodiments the inventive the oil-in-water emulsion includes at least one agriculturally active ingredient selected from the group consisting of: fungicides, insecticides, nematocides, miticides, biocides, termiticides, rodenticides, arthropodicides, herbicides, bactericides, and bacteria stats. In some embodiments the active ingredient is an herbicide selected from the group consisting of 2,4-D, aminopyralid, clopyralid, cyhalofop, fluroxypyr, haloxyfop, haloxyfop-P, picloram and triclopyr. In some embodiments the active ingredient is an insecticide selected from the group consisting of bifenthrin, chlorpyrifos, chlorpyrifos-methyl, cyfluthrin, beta-cyfluthrin, cyhalothrin, gamma-cyhalothrin, lambda-cyhalothrin, cypermethrin, alpha-cypermethrin, beta-cypermethrin, fenvalerate and permethrin. And in some embodiment the inventive formulation includes an active ingredient that is a fungicide selected from the group consisting of dinocap, fenbuconazole, meptyl dinocap, myclobutanil and propiconazole.

Some embodiments include methods of treating plants, comprising the steps of: providing an oil-in-water emulsion according to at least one other embodiment of the invention. In some embodiments the methods of treating plants, comprises the steps of: applying an oil-in-water emulsion according to the invention to a surface wherein the surface is a portion of at lest one plant and/or a surface adjacent to at least one plant.

DESCRIPTION

Some aspects of the present invention provide novel formulations of agriculturally active ingredients that include oil and water emulsion which demonstrate better stability than many currently available emulsion formulated for agricultural use. Some example, some aspect of the present invention include oil-in-water emulsion composition comprising:

an oil phase, which comprises oily globules comprising at least one compound which is agriculturally active; and an aqueous phase; wherein the oily globules are dispersed in the aqueous phase and stabilized by a polymeric adsorption layer which comprises: (1) at least one polymeric surface-active agent having an HLB value between 16 and 18, and (2) at least one ionic surface-active agent, and wherein the oily globules having a mean particle diameter of less than 800 nanometers.

Unless stated otherwise the term, 'about' as used herein means plus or minus 20 percent, e.g. about 2.0 includes values between 1.6 and 2.4.

The oil phase (A) of the oil-in-water emulsion of the present invention utilizes either an agriculturally active compound which is in the form of an oil, or alternatively, an agriculturally active compound dissolved or mixed in an oil, to form the oily globules. An oil is a liquid which is not miscible with water. In this invention, almost any oil which is compatible with the agriculturally active compound may be used in the oil-in-water emulsions of the present invention. Unless stated otherwise, the term 'compatible' means that the oil will dissolve or mix uniformly with the agriculturally active compound and allow for the formation of the oily globules of the oil-in-water emulsion of the present invention. Exemplary oils for this use include, but are not limited to, short-chain fatty acid triglycerides, silicone oils, petroleum fractions or hydrocarbons such as heavy aromatic naphtha solvents, light aromatic naphtha solvents, hydrotreated light petroleum distillates, paraffinic solvents, mineral oil, alkylbenzenes, paraffinic oils, and the like; vegetable oils such as soy oil, rape seed oil, coconut oil, cotton seed oil, palm oil, soybean oil, and the like; alkylated vegetable oils and alkyl esters of fatty acids such as methyloleate and the like.

Unless clearly stated or implied, an agriculturally active compound is herein defined as any oil, oil soluble and/or hydrophobic compound which exhibits at least some pesticidal or biocidal activity; and it is understood to refer to the active compound per se when it is itself an oil or alternatively, the active compound is dissolved in an oil. Such compounds or pesticides include fungicides, insecticides, nematocides, miticides, termiticides, rodenticides, arthropodicides, herbicides, biocides and the like. Examples of such agriculturally active ingredients can be found, for example, in The Pesticide Manual, 12th Edition. Exemplary pesticides which can be utilized in the oil-in-water emulsion of the present invention include, but are not limited to, benzofuranyl methylcarbamate insecticides such as benfuracarb, and carbosulfan; oxime carbamate insecticides such as aldicarb; fumigate insecticides such as chloropicrin, 1,3-dichloropropene and methyl bromide; juvenile hormone mimics such as fenoxycarb; organophosphate insecticides such as dichlorvos; aliphatic organothiophosphate insecticides such as malathion and terbufos; aliphatic amide organothiophosphate insecticides such as dimethoate; benzotriazine organothiophosphate insecticides such as azinphos-ethyl and azinphos-methyl; pyridine organothiophosphate insecticides such as chlorpyrifos and chlorpyrifos-methyl; pyrimidine organothiophosphate insecticides such as diazinon; phenyl organothiophosphate insecticides such as parathion and parathion-methyl; pyrethroid ester insecticides such as bifenthrin, cyfluthrin, beta-cyfluthrin, cyhalothrin, gamma-cyhalothrin, lambda-cyhalothrin, cypermethrin, alpha-cypermethrin, beta-cypermethrin, fenvalerate, and permethrin; and the like.

Exemplary herbicides which can be used in the oil-in-water emulsion of the present invention include, but are not limited to: amide herbicides such as dimethenamid and dimethenamid-P; anilide herbicides such as propanil; chloroacetanilide herbicides such as acetochlor, alachlor, butachlor, metolachlor and S-metolachlor; cyclohexene oxime herbicides such as sethoxydim; dinitroaniline herbicides such as benfluralin, ethalfluralin, pendimethalin, and trifluralin; nitrile herbicides such as bromoxynil octanoate; phenoxyacetic herbicides such as 4-CPA, 2,4-D, 3,4-DA, MCPA, and MCPA-thioethyl; phenoxybutyric herbicides such as 4-CPB, 2,4-DB, 3,4-DB, and MCPB; phenoxypropionic herbicides such as cloprop, 4-CPP, dichlorprop, dichlorprop-P, 3,4-DP, fenoprop, mecoprop and mecoprop-P; aryloxyphenoxypropionic herbicides such as cyhalofop, fluazifop, fluazifop-P, haloxyfop, haloxyfop-P; pyridine herbicides such as aminopyralid, clopyralid, fluroxypyr, picloram, and triclopyr; triazole herbicides such as carfentrazone ethyl; and the like.

Many of the herbicides that can be used to practice the invention can also generally be employed in combination with known herbicide safeners such as: benoxacor, cloquintocet, cyometrinil, daimuron, dichlormid, dicyclonon, dietholate, fenchlorazole, fenchlorazole-ethyl, fenclorim, flurazole, fluxofenim, furilazole, isoxadifen, isoxadifen-ethyl, mefenpyr, mefenpyr-diethyl, MG191, MON4660, 829148, mephenate, naphthalic anhydride, N-phenylsulfonylbenzoic acid amides and oxabetrinil.

Exemplary fungicides which can be used in the oil-in-water emulsion of the present invention include, but are not limited to, difenoconazole, dimethomorph, dinocap, diphenylamine, dodemorph, edifenphos, fenarimol, fenbuconazole, fenpropimorph, meptyl dinocap, myclobutanil, propiconazole, tebuconazole and the like.

It is understood by those skilled in the art that any combination of agriculturally active compounds may also be used in the oil-in-water emulsion of the present invention as long as a stable and effective emulsion is still obtained.

The amount of agriculturally active ingredient within the oil-in-water emulsion will vary depending upon the actual active ingredient, the application of the agriculturally active ingredient and the appropriate application levels which are well known to those skilled in the art. Typically, the total amount of agriculturally active ingredient within the oil-in-water emulsion will be from about 1, generally from about 5, preferably from about 10, more preferably from about 15 and most preferably from about 20 to about 45, generally to about 40, preferably to about 35 and most preferably to about 30 weight percent based on the total weight of the oil-in-water emulsion.

The polymeric surface-active agent in some embodiments has an HLB in the range of about 16 and about 18. The acronym HLB refers to the term "Hydrophilic Lipophilic Balance" which identifies an emulsifier's solubility in water or oil. Polymeric surface-active agents which can be used in the oil-in-water emulsion of the present invention include amphipathic block or graft copolymers. Preferred polymer surfactants are, but not limited to, EO/PO block copolymers. Block copolymers of ethylene-oxide (EO) and propylene-oxide (PO), as well as copolymers of EO and PO from ethylene diamine, are available in a variety of formulas and from a variety of sources, including the T'etronic™ and Pluronic™ polymers from BASF™, the Toximul™ polymers from Stepan™, the Atlas™ polymers from Uniqema™, the HartpoX™ polymers from Huntsman Corporation, as well as other sources.

The following is a non-limiting description of the nonionic block copolymers that may be useful herein. Structurally, nonionic block copolymers are characterized by an EO-PO-EO arrangement. They may have a total hydrophile (EO) content of about at least 30% or higher of the total molecular weight. The hydrophilic/lipophilic balance (HLB) of the nonionic block copolymers is about 16 to 18. The molecular weight of the polymeric surfactant is usually around 2000 to 15,000, preferably around 3000 to 8,000. Examples of preferable EO-PO polymers are, but not limited to, Toximul™ 8323, Atlas™ G5000, Pluronic™ P105, and Pluronic™ P85.

In addition to the polymeric surface-active agent, an ionic surface-active agent (2) also comprises the polymeric adsorption layer that is physically adsorbed onto the outer surface of oily globule. Ionic surface-active agents which can be used in the oil-in-water emulsion of the present invention include compounds such as (a) neutralized anionic surface-active agents, (b) amphoteric surface-active agents, (c) alkylsulphonic derivatives and (d) cationic surface-active agents.

Neutralized anionic surface-active agents (a) include, but are not limited to, for example: alkali metal salts of dicetyl phosphate and dimyristyl phosphate, in particular sodium and potassium salts; alkali metal salts of cholesteryl sulphate and cholesteryl phosphate, especially the sodium salts; lipoamino acids and their salts, such as mono- and disodium acylglutamates, such as the disodium salt of N-stearoyl-L-glutamic acid, the sodium salts of phosphatidic acid; phospholipids; and the mono- and disodium salts of acylglutamic acids, in particular N-stearoylglutamic acid.

Some anionic surface-active agents chosen from alkyl ether citrates and mixtures thereof which can be used in the oil-in-water emulsions of the present invention are disclosed in U.S. Pat. No. 6,413,527, which is incorporated herein by reference. Alkyl ether citrates include monoesters or diesters formed by citric acid and at least one oxyethylenated fatty alcohol comprising a saturated or unsaturated, linear or branched alkyl chain having from 8 to 22 carbon atoms and comprising from 3 to 9 oxyethylene groups, and mixtures thereof. Citrates that can be used to practice the invention include those chosen from the group consisting of, mono- and diesters of citric acid and of ethoxylated lauryl alcohol comprising from 3 to 9 oxyethylene groups. The alkyl ether citrates are preferably employed in the neutralized form at a pH of about 7. Neutralization agents can be chosen from inorganic bases, such as sodium hydroxide, potassium hydroxide or ammonia, and organic bases, such as mono, -di- and triethanolamine, aminomethyl-1,3-propanediol, N-methylglucamine, basic amino acids, such as arginine and lysine and mixtures thereof.

Amphoteric surface-active agents (b) include, but are not limited to, phospholipids and especially phosphatidylethanolamine from pure soya.

Alkylsulphonic derivatives (c) include, but are not limited to compounds of the formula:

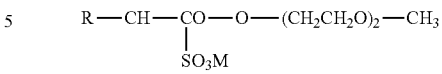

wherein R represents the radicals C16H33 and C18H37, taken as a mixture or separately, and M is an alkali metal, preferably sodium.

Cationic surface-active agents (d) include, but are not limited to, surface-active agents such as those disclosed in U.S. Pat. No. 6,464,990, which is incorporated herein by reference. They are typically selected from the group of quaternary ammonium salts, fatty amines and salts thereof. The quaternary ammonium salts include, for example, those which exhibit the following formula:

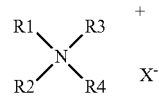

wherein the R1 to R4 radicals, which can be identical or different, represent a linear or branched aliphatic radical comprising from 1 to 30 carbon atoms or an aromatic radical, such as aryl or alkylaryl. The aliphatic radicals can comprise heteroatoms, such as oxygen, nitrogen, sulfur and halogens. The aliphatic radicals include alkyl, alkoxy, polyoxy(C2-C6)alkylene, alkylamido, (C12-C22)alkyl-amido(C2-C6) alkyl, (C12-C22)alkyl acetate and hydroxyalkyl radicals comprising approximately from 1 to 30 carbon atoms; X is an anion selected from halides, phosphates, acetates, lactates, (C2-C6) alkyl sulfates, and alkyl- or alkylarylsulfonates. Preference is given, as quaternary ammonium salts to tetraalkylammonium chlorides, such as dialkyldimethylammonium and alkyltrimethylammonium chlorides in which the alkyl radical comprises approximately from 12 to 22 carbon atoms, in particularly behenyltrimethyl-ammonium, distearyldimethylammonium, cetyltrimethylammonium and benzyldimethylstearylammonium chlorides, or alternatively, stearamidopropyl-dimethyl(myristyl acetate) ammonium chloride; imidazolinium quaternary ammonium salts, such as those of formula:

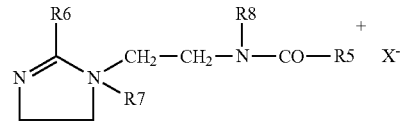

wherein R5 represents an alkenyl or alkyl radical comprising from 8 to 30 carbon atoms, for example derived from tallow fatty acids; R6 represents a hydrogen atom, an alkyl radical comprising from 1 to 4 carbon atoms or an alkenyl or alkyl radical comprising from 8 to 30 carbon atoms; R7 represents an alkyl radical comprising from 1 to 4 carbon atoms; R8 represents a hydrogen atom or an alkyl radical comprising from 1 to 4 carbon atoms; and X is an anion selected from the group of the halides, phosphates, acetates, lactates, alkyl sulfates, or alkyl, and alkylarylsulfonates. R5 and R6 preferably denote a mixture of alkenyl or alkyl radicals comprising from 12 to 21 carbon atoms, for example, derived from tallow fatty acids, R7 preferably denotes a methyl radical and R8 preferably denotes hydrogen. Quaternary diammonium salts are also contemplated, such as propanetallowdiammonium dichloride.

Fatty amines include, but are not limited to those of formula:

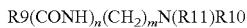
R9(CONH)$_n$(CH$_2$)$_m$N(R11)R10 wherein R9 is an optionally saturated and/or branched hydrocarbon chain, having between 8 and 30 carbon atoms, preferably between 10 and 24 carbon atoms; R10 and R11 are selected from H and an optionally saturated and/or branched hydrocarbon chain, having between 1 and 10 carbon atoms; preferably between 1 and 4 carbon atoms; m is an integer between 1 and 10 and is preferably between 1 and 5; and n is either 0 or 1.

Examples of fatty amines that can be used to practice the invention include, but are not limited to, stearylamine, aminoethyl-ethanolamide stearate, diethylenetriamine stearate, palmitamidopropyldimethyl-amine, palmitamidopropyldiethylamine, palmitamidoethyldiethylamine, palmitamidoethyldimethylamine Commercially available fatty amines include, but are not limited to, Incromine™ BB from Croda, Amidoamine™ MSP from Nikkol, and Lexamine™ series from Inolex, the Acetamine series from Kao Corp; Berol 380, 390, 453 and 455, and Ethomeen™ series from Akzo Nobel, and Marlazin™ L10, OL2, OL20, T15/2, T50 from Condea Chemie.

The surface-active agents of (1) and (2) form a polymeric adsorption layer surrounding the oily globules suspended within the aqueous phase of the oil-in-water emulsion of the present invention. The amount of the surface-active agents (1) utilized in the oil-in-water emulsion of the present invention is typically from 0.1 to 20, preferably from about 0.5 to about 10, and more preferably to about 2 weight percent, based on the total weight of the oil-in-water emulsion. The amount of the surface-active agents (2) utilized in the oil-in-water emulsion of the present invention is typically from 0.1 to 20, preferably from about 0.2 to about 5, and more preferably to about 0.5 weight percent, based on the total weight of the oil-in-water emulsion.

The ratio of the total weight of the surface-active compounds (1) and (2) to the total weight of oil is typically from about 1:2.5 to about 1:30.

The aqueous phase (B) is typically water, for example, deionized water. The aqueous phase may also contain other additives such as compounds that lower the freezing point, for example, alcohols, e.g., isopropyl alcohol and propylene glycol; pH buffering agents, for example, alkali phosphates such as sodium phosphate monobasic monohydrate, sodium phosphate dibasic; biocides, for example, Proxel GXL; and antifoams, for example octamethylcyclotetrasiloxane (Antifoam A from Dow Corning). Other additives and/or adjuvants can also be present in the aqueous phase (B) as long as the stability of the oil-in-water emulsion is still maintained. Other additives also include water-soluble agriculturally active compounds.

The oil phase or the coated oily globules are typical from about 0.1 to about 55, preferably from about 10 to about 50, and more preferably from about 20 to about 45 percent, and most preferably from about 30 to about 40 weight percent, based on the total weight of the oil-in-water emulsion composition. The oil/water ratio is typically less than or equal to 1.

Other additives and/or adjutants can also be present within the oil-in-water emulsion of the present invention, as long as the stability and activity of the oil-in-water emulsion is still obtained. Some of the oil-in-water emulsions of the present invention may contain additional polymeric surface-active agents (3) to improve the performace of the emulsions such as the emulsion stability, and low temperature stability performance. Suitable polymer surface-active agents may include, but are not limited to, non ionic polymeric surfactants with HLB value from 12 to 14, such as Soprophor™ 796/P (Ethopropoxylated Polyarylphenol from Rhodia). Some of the oil-in-water emulsions of the present invention may additionally contain adjuvant surface-active agents to enhance deposition, wetting and penetration of the agriculturally active ingredient onto the target site, e.g., crop, weed or organism. These adjuvant surface-active agents may optionally be employed as a component of the emulsion in either phase A or B, or as a tank mix component; the use of and amount desired being well known by those skilled in the art. Suitable adjuvant surface-active agents include, but are not limited to, ethoxylated nonyl phenols, ethoxylated synthetic or natural alcohols, salts of the esters or sulphosuccinic acids, ethoxylated organosilicones, ethoxylated fatty amines and blends of surface-active agents with mineral or vegetable oils.

The oil-in-water emulsion of the present invention can be prepared, in part, according to the process described in U.S. Pat. No. 5,925,364, the teachings of which are incorporated herein by reference. The mixture may be homogenized by cavitations using a high pressure homogenizer, to provide the small particle sized oily globules. The mean size of the coated oily globules is typically less than about 800 nanometers, preferably less than about 500 nanometers and more preferably about 200 nanometers, as determined using laser diffraction particle size analysis and scanning electron microscopy.

In one embodiment, the oil-in-water emulsion is prepared by: mixing 1) (A) an oil phase, an agriculturally active compound and optionally an oil and (B) an aqueous phase, comprising water, the polymeric surfactant(s) and the ionic surfactant(s), to obtain a mixture; and 2) homogenizing the mixture, for example, by subjecting the mixture to cavitation.

In the first step, the mixture can be formed by conventional stirring, for example, using a high shear homogenizer rotating at a rate of approximately between 2000 and 7000 rpm for a time period of between about 5 to about 15 minutes and at a temperature of between approximately 20° C. and 50° C.

The homogenization step may be performed by using a high pressure homogenizer operating at pressures between approximately 200 and 1000 bar as is well known to those skilled in the art. The process may be performed by successive passages, generally from 1 to 4 passages, at an elevated pressure; the mixture gradually being returned to normal (generally ambient) pressure between each passage. The homogenization of the second step may also be carried out using other techniques such as ultrasound or by the use of a homogenizer equipped with a rotor-stator type head.

Other embodiments of the present invention may include the use of the oil-in-water emulsion in agricultural applications to control, prevent or eliminate unwanted living organisms, e.g., fungi, weeds, insects, bacteria or other microorganisms and other pests. This use includes its use for protecting a plant against attack by a phytopathogenic organism or the treatment of a plant already infested by a phytopathogenic organism, comprising the step applying the oil-in-water emulsion composition, to soil, a plant, a part of a plant, foliage, flowers, fruit, and/or seeds, or any surface adjacent to a plant in a disease inhibiting and phytologically acceptable amount. The term "disease inhibiting and phytologically acceptable amount" refers to an amount of a compound that kills or inhibits the plant disease for which control is desired, in an amount not significantly toxic to the plant being treated. The exact concentration of active compound required varies with the fungal disease to be controlled, the type of formulations employed, the method of application, the particular plant species, climate conditions, and the like, as is well known in the art.

Additionally, the oil-in-water emulsions of the present invention are useful for the control of insects or other pests, e.g., rodents. Therefore, the present invention also is directed to a method for inhibiting an insect or other pest, such as mites, which comprises applying to a locus of the insect or pest an oil-in-water emulsion comprising an insect-inhibiting amount of an agriculturally active compound for such use. The "locus" of insects or pests is a term used herein to refer to the environment in which the insects or other pests live or where their eggs are present, including the air surrounding them, the food they eat, or objects which they contact. For example, insects which eat or contact crop or other desirable plants can be controlled by applying the active compound to plant parts such as the seed, seedling, or cutting which is planted, the leaves, stems, fruits, grain, or roots, to the soil in which the roots are growing or to any surfaces adjacent to the desirable plants. It is contemplated that the agriculturally active compounds and oil-in-water emulsions containing such, might also be useful to protect textiles, paper, stored grain, seeds, domesticated animals, buildings or human beings by applying an active compound to or near such objects. The term "inhibiting an insect or pest" refers to a decrease in the numbers of living insects or other pests in any stage of their life cycle, or a decrease in the number of viable insect or other pest eggs. The extent of reduction accomplished by a compound depends, of course, upon factors including the application rate of the compound, the particular compound used, and the target insect or pest species and the like. At least an inactivating amount should be used in at least one application of the material. The terms "insect or pest-inactivating amount" are used to describe the amount, which is sufficient to cause a measurable reduction in the treated insect or pest population, as is well known in the art.

The locus to which a compound or composition is applied can be any locus inhabited by an insect, mite or pest, for example, vegetable crops, fruit and nut trees, grape vines, ornamental plants, domesticated animals, plants grown for fuel, wood or fiber, the interior or exterior surfaces of buildings, and the soil around buildings.

Because of the unique ability of insect eggs and other pest lain eggs to resist toxicant action, as is true of many insecticides and acaricides, repeated applications may be desirable to control newly emerged larvae.

Additionally, the present invention relates to the use of oil-in-water emulsions comprising agriculturally active compounds which are herbicides. The term herbicide is used herein to mean an active ingredient that kills, controls or otherwise adversely modifies the growth of at least one type of plant. An herbicidally effective or vegetation controlling amount of an herbicide is an amount of active ingredient which causes an adversely modifying effect and includes deviations from natural development of the plant, killing, regulation, desiccation, retardation, and the like. The terms "plants" and "vegetation" include emerging seedlings as well as established and dormant vegetation.

Herbicidal activity may be exhibited when the compound(s) are applied directly to the locus of an undesirable plant thereof at any stage of growth or before emergence of the weeds. The effect observed depends upon factors such as the plant species to be controlled, the stage of growth of the plant, the particle size of solid components, the environmental conditions at the time of use, the specific adjuvants and carriers employed, the soil type, and the like, as well as the amount of chemical applied. These and other factors can be adjusted, as is known in the art, to promote selective herbicidal action. Generally, it is preferred to apply such herbicides post emergence or to relatively immature undesirable vegetation to achieve the maximum control of weeds.

Still other aspects of the present invention include methods of preventing or controlling pests such as nematodes, mites, arthropods, rodents, termites, bacteria or other microorganisms, comprising applying to a locus where control or prevention is desired a composition of the present invention which comprises the appropriate active compound such as a nematocide, miticide, arthropodicide, rodenticide, termiticide or biocide.

The actual amount of agriculturally active compound to be applied to loci of disease, insects and mites, weeds or other pests is well known in the art and can readily be determined by those skilled in the art in view of the teachings above.

The composition of the present invention surprisingly offers stable agricultural oil-in-water emulsions having low viscosity and long term shelf life. Additionally, the stable agricultural oil-in-water emulsions of the present invention can offer other surprising improvements, e.g., efficacy.

The following examples are provided to illustrate the present invention. The examples are not intended to limit the scope of the present invention and they should not be so interpreted. Amounts are in weight parts or weight percentages unless otherwise indicated.

The following examples are provided to further illustrate the invention and are not meant to be construed as limiting.

As disclosed herein, all temperatures are given in degrees Celsius and all percentages are weight percentages unless otherwise stated.

In the specific examples disclosed herein, the exemplary emulsions are created according to the following procedure:

Oil phase A and the aqueous phase B may be heated separately to their desired temperatures. Phase B is poured into Phase A, with stirring of 3000-7000 rpm provided by a Silverson L4RT high shear homogenizer fitted with a square hole high shear screen. Stirring and temperature conditions are maintained for about 5 to about 15 minutes.

The mixture is then introduced into a Niro Soavi high pressure 2-stage homogenizer of type Panda 2K, which is adjusted to a pressure of about 500 to about 1000 bar for 1 to 4 successive passages.

A stabilized oil-in-water emulsion is thus obtained, the oily globules of which have a mean diameter of typically about 200 nm.

The components of Formulation 1 are summarized in Table 1.

TABLE 1

35% soybean oil-in-water emulsion.

| Oil phase | weight percent (wt. %) |
| --- | --- |
| Soybean Oil | 35 |
| Aqueous phase | wt. % |
| Cedepal TD-407[1] | 0.5 |
| Atlas G5000[2] | 2.0 |
| Soprophor 796/P[3] | 0.25 |
| Propylene Glycol | 6.0 |
| Water (to balance) | |

[1]Sodium trideceth sulfate, available from Stepan, Northfield, Illinois
[2]Polyalkylene glycol ether, available from Croda Uniqema Inc., New Castle, Delaware
[3]Ethoproxylated polyaryl phenol, available from Rhodia, Cranberry, NJ Formulation 1 demonstrated excellent physical stability. For example, Formulation 1 was stable under accelerated storage test conditions of 8 weeks at about 54° C., and cycling temperature from about 40° C. to about −10° C. with no change in the size of the oily globules and no sedimentation or syneresis.

The components of Formulation 2 are summarized in Table 2.

Both exemplary Formulations 2 and 3, disclosed herein, were developed to demonstrate that the current invention may be combined with a vegetable oil modified phase to suppress Ostwald Ripening and deliver superior physical stability over storage.

TABLE 2

100 gae/l Fluroxypyr MHE + 100 gae/l Triclopyr BEE oil-in-water emulsion.

| | wt. % |
|---|---|
| Oil phase | |
| Triclopyr butoxyethylester (BEE) | 13.10 |
| Fluroxypyr methylheptylester (MHE) | 13.50 |
| Agnique AMD 810[4] | 4 |
| Soybean Oil | 4 |
| Aqueous phase | |
| Cedepal TD-407 | 0.5 |
| Toximul 8323[5] | 2 |
| Propylene Glycol | 10 |
| Water (balanced ingredient) | |

[4]$N_1$N-Dimethyldecanamide, available from Cognis, BASF Corporation, Cincinnati, OH
[5]Polyalkylene oxide block copolymer, available from Stepan, Northfield, IL Formulation 2 was stable under accelerated storage test conditions of 2 weeks at about 54° C., and cycling temperature from about 40° C. to about −10° C. with no change in the size of the oily globules and no sedimentation or syneresis.

The components of Formulation 3 are summarized in Table 3.

TABLE 3

65 gae/l Picloram isooctylester + 240 gae/l 2,4-D 2-ethyhexylester emulsion

| | wt % |
|---|---|
| Oil phase | |
| Picloram isooctylester | 9.52 |
| 2,4-D 2-ethyhexylester | 36.2 |
| Soybean oil | 4.0 |
| Aqueous phase | |
| Amisoft HS-21P[6] | 0.5 |
| Toximul 8223 | 2 |
| Soprophor 796/P | 0.5 |
| Proxel GXL[7] | 0.1 |
| $(NH_4)_2HPO_4$ | 0.5 |
| Propylene Glycol | 6 |
| Water (balanced ingredient) | |

[6]Disodium N-stearoyl-L-glutamate, available from Ajinomoto North America Inc, Fort Lee, NJ
[7]~19% 1,2-Benzisothia zolin-3-one, available from Arch Chemical, Inc., Atlanta, Georgia Formulation 3 was stable under accelerated storage test conditions of 2 weeks at about 54° C., and cycling temperature from about 40° C. to about −10° C. with no change in the size of the oily globules and no sedimentation or syneresis.

The components of Formulation 4 are summarized in Table 4.

Formulation 4 was designed to demonstrate the current invention has inherent salt tolerance stability. In this example, a Triclopyr butoxyethylester (BEE) emulsion without Aminopyralid Triisopropanolamine (TIPA) salt was first prepared. Next, the Triclopyr BEE emulsion was blended with an Aminopyralid TIPA pre-mixture including water and Propylene glycol to produce the final formulation.

TABLE 4

240 gae/l Triclopyr BEE + 30 gae/l Aminopyralid TIPA salt emulsion.

| | wt % |
|---|---|
| Oil phase | |
| Triclopyr BEE | 44.0 |
| Soybean oil | 4 |
| Aqueous phase | |
| Cedepal TD-407 | 0.5 |
| Toximul 8323 | 2.0 |
| Soprophor 796/P | 0.5 |
| Propylene Glycol | 6.0 |
| $(NH_4)_2HPO_4$ | 0.5 |
| Water (balanced ingredient) | |

The above emulsion was then blended with an Aminopyralid TIPA salt pre-mixture to create the formulation summarized in Table 5.

TABLE 5

Blended salt tolerant formulation (by weight percent).

| Triclopyr BEE | 29.44 |
|---|---|
| Aminopyralid TIPA | 5.52 |
| Propylene Glycol | 10 |
| Water plus ingredients listed in Table 4 (balanced ingredients) | |

The formulation disclosed in Table 5 was stable under accelerated storage test conditions of 4 weeks at about 54° C., and cycling temperature from about 40° C. to about −10° C. with no change in the size of the oily globules and no sedimentation or syneresis.

The components of Formulation 5 are summarized in Table 6.

Formulation 5 was designed in part to demonstrate that the current invention may be combined with the current oil-in-water technology as well as a polymer modified oil phase. The resulting formulation was stable during storage. The sample preparation process was similar to that of Formulation 4, described above.

TABLE 6

80 gae/l Fluroxypyr MHE + 40 gae/l Aminopyralid K salt Emulsion.

| | wt % |
|---|---|
| Oil phase | |
| Fluroxypyr MHE | 27.29 |
| Agnique AMD 810 | 20 |
| Ethocel 10[8] | 2.59 |
| Nikkol DGMS[9] | 2.7 |
| Tween 61 | 2.03 |

TABLE 6-continued

80 gae/l Fluroxypyr MHE + 40 gae/l Aminopyralid K salt Emulsion.

| | wt % |
|---|---|
| Aqueous phase | |
| Amisoft HS-21P | 0.53 |
| Propylene Glycol | 6.0 |
| Water (balanced ingredient) | |

[8]Ethylecellulose, available from Dow, Midland, Michigan
[9]Polyglyceryl-2 stearate, available from Nikkol, Tokyo, Japan Formulation 5 (Table 6) was first mixed with Toximul 8323 and Soprophor 796/P for 1-2 hours with good agitation. Then Aminopyralid potassium (K) salt pre-mixture (Aminopyralid K, Propylene Glycol, and water) was slowly added into the formulation with good agitation to make the final formulation which is shown in Table 7.

TABLE 7

Polymer modified oil phase blended formulation (by weight percent).

| Fluroxypyr MHE | 11.03 |
|---|---|
| Aminopyralid K[10] | 4.53 |
| Toximul 8323 | 2 |
| Soprophor 796/P | 0.5 |
| Propylene Glycol | 10 |
| Water plus ingredients from Table 6 (balance ingredients) | |

[10]2-pyridine carboxylic acid, 4 amino-3,6-dichloro, available from Dow AgroSciences, Indianapolis, Indiana The formulation of Table 7 was stable under accelerated storage test conditions of 5 weeks at about 54° C., and cycling temperature from about 40° C. to about −10° C. with no change in the size of the oily globules and no sedimentation or syneresis.

While the novel technology has been illustrated and described in detail in the figures and foregoing description, the same is to be considered as illustrative and not restrictive in character, it being understood that only some of the embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

What is claimed is:

1. An oil-in-water emulsion composition having at least one agriculturally active compound, the oil-in-water emulsion composition comprising:
    A) an oil phase, wherein the oil phase includes at least one agriculturally active ingredient, said oil phase comprising oily globules, the oily globules having a mean particle diameter of less than about 800 nanometers; and
    B) an aqueous phase, wherein the oily globules are dispersed in the aqueous phase and wherein at least some of the oily globules dispersed in the aqueous phase are coated with a polymeric adsorption layer, wherein said polymeric adsorption layer consists of:
        (1) at least one polymeric surface-active agent having an HLB value in the range of about 16 to about 18; and
        (2) at least one ionic surface-active agent.

2. The composition of claim 1 wherein the aqueous phase includes a second polymeric surface active agent having an HLB in the range of about 12 to about 14.

3. The composition of claim 1 wherein the polymeric surface-active agent is selected from the group consisting of: amphipathic block and graft copolymers.

4. An oil-in-water emulsion composition having at least one agriculturally active compound, the oil-in-water emulsion composition comprising:
    A) an oil phase, wherein the oil phase includes at least one agriculturally active ingredient, said oil phase comprising oily globules, the oily globules having a mean particle diameter of less than about 800 nanometers; and
    B) an aqueous phase, wherein the oily globules are dispersed in the aqueous phase and wherein at least some of the oily globules dispersed in the aqueous phase are coated with a polymeric adsorption layer, wherein said polymeric adsorption layer consists of:
        (1) at least one polymeric surface-active agent having an HLB value in the range of about 16 to about 18;
        (2) at least one ionic surface-active agent; and
        (3) at least one adjuvant surface active agent selected from the group consisting of: ethoxylated nonyl phenols, ethoxylated synthetic or natural alcohols, salts of the esters or sulphosuccinic acids, ethoxylated organosilicones, and ethoxylated fatty amines.

5. The composition of claim 1 wherein the ionic surface-active agent is selected from the group consisting of: (a) neutralized anionic surface-active agents, (b) amphoteric surface-active agents, (c) alkylsulphonic derivatives and (d) cationic surface-active agents.

6. The composition of claim 4, wherein the ionic surface-active agent is selected from the group consisting of: alkali metal salts of dicetyl phosphate and dimyristyl phosphate; alkali metal salt of cholesteryl sulphate and cholesteryl phosphate; lipoamino acids and their salts; phospholipids; the mono- and disodium salts of acylglutamic acid; and alkyl ether citrates.

7. The composition of claim 1, wherein the ionic surface-active agent is a phospholipid.

8. The composition of claim 1 wherein the ionic surface-active agent is an alkylsulphonic derivative.

9. The composition of claim 1 wherein the ionic surface-active agent is selected from the group consisting of quaternary ammonium salts, fatty amines and salts thereof.

10. The composition of claim 1, wherein the amount of the polymeric surface-active agents (1) in the composition is in the range of about 30 to about 95, wt. % of the total of both (1) and (2).

11. The composition of claim 1, wherein the amount of the polymeric surface-active agents (1) in the composition is in the range of about 50 to about 95, weight percent of the total of both (1) and (2).

12. The composition of claim 1, wherein the amount of the ionic surface active agent (2) in the composition is in the range of about 5 to about 50 wt. % of the total combined weight of (1) and (2).

13. The composition of claim 1, wherein the amount of the ionic surface active agent (2) in the composition is in the range of about 10 to about 50 wt. % of the total combined weight of (1) and (2).

14. The composition of claim 1, wherein the coating on the oily globules comprises between about 0.5 wt. % to about 20 wt. % based on the total weight of the oil-in-water emulsion.

15. The composition of claim 1, wherein the coating on the oily globules comprises between about 0.5 wt. % to about 10 wt. % based on the total weight of the oil-in-water emulsion.

16. The composition of claim 1, wherein the coating on the oily globules comprises between about 0.5 wt. % to about 2.5 wt. % based on the total weight of the oil-in-water emulsion.

17. The composition of claim 1, wherein the oil-in-water emulsion includes at least one agriculturally active ingredient selected from the group consisting of: fungicides, insecticides, nematocides, miticides, biocides, termiticides, rodenticides, arthropodicides, herbicides, bactericides, and bacteria stats.

18. The composition of claim 17, wherein the active ingredient is an herbicide selected from the group consisting of 2,4-D, aminopyralid, clopyralid, cyhalofop, fluroxypyr, haloxyfop, haloxyfop-P, picloram and triclopyr.

19. The composition of claim 17, wherein the active ingredient is an insecticide selected from the group consisting of bifenthrin, chlorpyrifos, chlorpyrifos-methyl, cyfluthrin, beta-cyfluthrin, cyhalothrin, gamma-cyhalothrin, lambda-cyhalothrin, cypermethrin, alpha-cypermethrin, beta-cypermethrin, fenvalerate and permethrin.

20. The composition of claim 17, wherein the active ingredient is a fungicide selected from the group consisting of dinocap, fenbuconazole, meptyl dinocap, myclobutanil and propiconazole.

21. A method of treating a plant, comprising the steps of: applying an oil-in-water emulsion according to claim 1 to a surface.

22. The method according to claim 21, wherein the surface is the surface of a plant.

23. The method according to claim 21, wherein the surface is adjacent to a plant.

24. The method according to claim 21, wherein the surface is a surface of a plant pest or a plant pathogen.

25. An oil-in-water emulsion composition having at least one agriculturally active compound, the oil-in-water emulsion composition comprising:
   A) an oil phase, wherein the oil phase includes at least one agriculturally active ingredient, said oil phase comprising oily globules, the oily globules having a mean particles diameter of less that about 800 nanometers; and
   B) an aqueous phase, wherein the oily globules are dispersed in the aqueous phase and wherein at least some of the oily globules dispersed in the aqueous phase are coated with a polymeric adsorption layer, wherein said polymeric adsorption layer consists of:
      (1) at least one polymeric surface-active agent having an HLB value in the range of about 16 to about 18;
      (2) at least one ionic surface-active agent;
      (3) at least one second polymeric surface active agent having an HLB in the range of about 12 to about 14.

\* \* \* \* \*

UNITED STATES PATENT AND TRADEMARK OFFICE
CERTIFICATE OF CORRECTION

PATENT NO. : 8,835,357 B2
APPLICATION NO. : 13/349171
DATED : September 16, 2014
INVENTOR(S) : Ouse et al.

Page 1 of 1

It is certified that error appears in the above-identified patent and that said Letters Patent is hereby corrected as shown below:

In the Claims,

Claim 6, Column 14, Line 35, amend as follows:

please change [claim 4] to claim 1

Signed and Sealed this
Thirtieth Day of December, 2014

Michelle K. Lee
*Deputy Director of the United States Patent and Trademark Office*